US010100267B1

(12) United States Patent
Moretti et al.

(10) Patent No.: US 10,100,267 B1
(45) Date of Patent: Oct. 16, 2018

(54) GREEN, LILY OF THE VALLEY PERFUMING INGREDIENT

(71) Applicant: Firmenich SA, Geneva (CH)

(72) Inventors: Robert Moretti, Geneva (CH); Anthony Alexander Birkbeck, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 15/758,589

(22) PCT Filed: Sep. 13, 2016

(86) PCT No.: PCT/EP2016/071531
§ 371 (c)(1),
(2) Date: Mar. 8, 2018

(87) PCT Pub. No.: WO2017/046071
PCT Pub. Date: Mar. 23, 2017

(30) Foreign Application Priority Data

Sep. 16, 2015 (EP) ..................................... 15185462

(51) Int. Cl.
A61K 8/00 (2006.01)
C11B 9/00 (2006.01)
C07C 47/225 (2006.01)

(52) U.S. Cl.
CPC .......... C11B 9/0034 (2013.01); C07C 47/225 (2013.01); C07C 2601/16 (2017.05)

(58) Field of Classification Search
USPC ................................................. 512/22, 8, 1
See application file for complete search history.

(56) References Cited

U.S. PATENT DOCUMENTS

| 4,396,670 | A | 8/1983 | Sinclair | |
|---|---|---|---|---|
| 2009/0036347 | A1* | 2/2009 | Levorse, Jr. | A61K 8/33 512/8 |
| 2013/0090390 | A1* | 4/2013 | Singer | A61Q 13/00 514/772 |

FOREIGN PATENT DOCUMENTS

| EP | 1054053 A2 | 11/2000 |
|---|---|---|
| JP | 50094143 | 7/1975 |
| WO | WO2001041915 | 6/2001 |
| WO | WO2008053148 | 5/2008 |

OTHER PUBLICATIONS

Fehr et al, Synthesis of (−)Cubebol by Face-Selective Platinum, Gold, or Copper Catalyzed Cycloisomerization: Evidence of Chirality Transfer and Mechanistic Insights, 2009, Chem. Eur. J., 15, 9773-9784 (Year: 2009).*
International Search Report and Written Opinion, application PCT/EP2016/071531 dated Nov. 29, 2016.
Bone et al. 'Microencapsulated Fragrances in Melamine Formaldehyde Resins', Chimia, 2011, vol. 65, n° 3, pp. 177-181.
Dietrich et al., 'Amino resin microcapsules. I. Literature and patent review', Acta Polymerica, vol. 40 (1989), n° 4, pp. 243-251.
Dietrich et al., 'Amino resin microcapsules. II. Preparation and morphology', Acta Polymerica, vol. 40 (1989), n° 5, pp. 325-331.
Dietrich et al., 'Amino resin microcapsules. III. Release properties', Acta Polymerica, vol. 40 (1989), n° 11, pp. 683-690.
Dietrich et al., 'Amino resin microcapsules. IV. Surface tension of the resins and mechanism of capsule formation', Acta Polymerica, vol. 41 (1990), n° 2, pp. 91-95.
Jackman et al., 'Synthesis and Chiroptical Properties of Some Piperidin-2-ones', J. Org. Chem. 1982, vol. 47, pp. 1824-1831.
Lee et al., 'Microencapsulation of fragrant oil via in situ polymerization . . . ', J. Microencapsulation, 2002, vol. 19, No. 5, pp. 559-569.
Mehta et al., 'Terpenes to Terpenes. Stereo- and Enantio-selective Synthesis of (+)-alph-Elemene . . . ', J. Chem. Soc., Chem. Commun., 1994, pp. 2759-2760.

* cited by examiner

Primary Examiner — Jessica Whiteley
(74) Attorney, Agent, or Firm — Winston & Strawn LLP

(57) ABSTRACT

The present invention concerns compound of formula (I)

in the form of any one of its stereoisomers or a mixture thereof, and wherein the exocyclic dotted line represents a carbon-carbon single or double bond, and one endocyclic dotted to line represents a carbon-carbon single bond and the other endocyclic dotted line represents a carbon-carbon double bond; and R, $R^1$ and $R^2$ represent, independently from each other, a hydrogen atom or a $C_{1-3}$ alkyl group; and their use in perfumery to impart odor notes of the green, floral type.

18 Claims, No Drawings

GREEN, LILY OF THE VALLEY PERFUMING INGREDIENT

RELATED APPLICATIONS

This application is a national stage application under 35 U.S.C. § 371 filing of International Patent Application PCT/EP2016/071531, filed Sep. 13, 2016, which claims the benefit of European patent application n° 15185462.7 filed Sep. 16, 2015.

TECHNICAL FIELD

The present invention relates to the field of perfumery. More particularly, it concerns the use as perfuming ingredient of compounds of formula (I) as defined below, which are useful perfuming ingredients of the green, floral type. Therefore, following what is mentioned herein, the present invention comprises the invention's compound as part of a perfuming composition or of a perfuming consumer product.

BACKGROUND

To the best of our knowledge, the compounds of formula (I) are novel.

To the best of our knowledge, some structural analogues are reported as perfuming ingredients.

WO 08/053148 reports some cyclohexyl (i.e. saturated) analogues of the present invention which are described as having perfuming properties of the lily of the valley type. Said document does not suggest unsaturated compounds, and the only compounds having also green note do have a significantly different substitution pattern compared to the present ones.

US 2009/0036347 discloses also cyclohexyl (i.e. saturated) analogues of the present invention (in particular 3-(3-isopropylcyclohexyl)propanal) as having orris, earthy and fatty odor note, so perfuming properties very different from the one of the present invention.

Therefore, none of these documents reports or suggests any organoleptic properties of the compounds of formula (I), or any use of said compounds in the field of perfumery.

DESCRIPTION OF THE INVENTION

We have now surprisingly discovered that a cyclohexenyl compound of formula

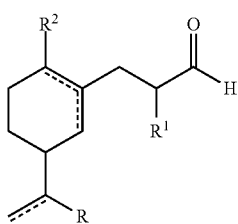

(I)

in the form of any one of its stereoisomers or a mixture thereof, and wherein the exocyclic dotted line represents a carbon-carbon single or double bond, and one endocyclic dotted line represents a carbon-carbon single bond and the other endocyclic dotted line represents a carbon-carbon double bond; and
R, $R^1$ and $R^2$ represent, independently from each other, a hydrogen atom or a $C_{1-3}$ alkyl group;

can be used as perfuming ingredient, for instance to impart odor notes of the green, floral type.

For the sake of clarity, by the expression "any one of its stereoisomers", or the similar, it is meant the normal meaning understood by a person skilled in the art, i.e. that the invention's compound can be a pure enantiomer (if chiral) or diastereomer (e.g. the ring substituent is in a conformation syn or anty).

For the sake of clarity, by the expression "wherein . . . dotted line represents a carbon-carbon single bond or double bond . . . ", or the similar, it is meant the normal meaning understood by a person skilled in the art, i.e. that the whole bonding (solid and dotted line) between the carbon atoms connected by said dotted line is a carbon-carbon single or double bond, provided that only one cyclic dotted line is a double bond.

For the sake of clarity, by the expression "endocyclic" it is meant the normal meaning understood by a person skilled in the art, i.e. that the whole bonding is located within the cyclic moiety. Similarly, by the expression "exocyclic" it is meant the normal meaning understood by a person skilled in the art, i.e. that the whole bonding is located outside the cyclic moiety.

According to a particular embodiment of the invention, said compound (I) is a compound of formula

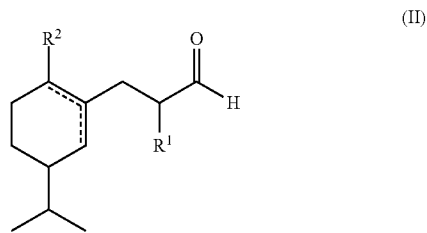

(II)

wherein one dotted line represents a carbon-carbon single bond and the other dotted line represents a carbon-carbon double bond, and $R^1$ and $R^2$ have the same meaning indicated in formula (I).

According to any one of the above embodiments of the invention, said invention's compounds are $C_{12}$-$C_{14}$ compounds.

According to any one of the above embodiments of the invention, said R is a hydrogen atom or a methyl or ethyl group, in particular a methyl group.

According to any one of the above embodiments of the invention, said $R^1$ is a hydrogen atom or a methyl or ethyl group, in particular a hydrogen atom or a methyl group.

According to any one of the above embodiments of the invention, said $R^2$ is a hydrogen atom or a methyl or ethyl group, in particular a hydrogen atom or a methyl group.

According to any one of the above embodiments of the invention, one of said $R^1$ or $R^2$ is a hydrogen atom and the other is a hydrogen atom or a methyl group.

According to any one of the above embodiments of the invention, said $R^1$ and $R^2$ are each a hydrogen atom.

According to any one of the above embodiments of the invention, said $R^1$ is a hydrogen atom and $R^2$ is a methyl group.

As specific examples of the invention's compounds, one may cite, as non-limiting example, 3-[5-(2-propanyl)-1-cyclohexen-1-yl]propanal and/or its isomer 3-[3-(2-propanyl)-1-cyclohexen-1-yl]propanal which are characterized by an odor having very powerful fresh green and floral (lily of the valley type) notes duality comprising also citrus and violet leaves/pyrazine aspects. Said compounds can impart an astonishing green freshness allied with a remarkable substantivity, a rare combination for perfumery ingredients. Said green note has a clear sap, watery connotation.

According to a particular embodiment of the invention, the mixtures of said 3-[5-(2-propanyl)-1-cyclohexen-1-yl]propanal and its isomer 3-[3-(2-propanyl)-1-cyclohexen-1-yl]propanal are particularly appreciated for their olfactive performances.

As other specific, but non-limiting, examples of the invention's compounds, one may cite the following ones in Table 1:

TABLE 1

Invention's compounds and their odor properties

| Compound structure and name | Odor notes |
|---|---|
| 3-[(5S)-5-isopropyl-2-methyl-1-cyclohexen-1-yl]propanal | Strong green, floral notes with aldehyde and watery aspects |
| 3-[(5R)-5-isopropyl-2-methyl-1-cyclohexen-1-yl]-2-methylpropanal | Fresh citrus, green, floral notes |
| 3-[5-ethyl-1-cyclohexen-1-yl]propanal | Green, ozone, floral/lily of the valley |
| 3-(5-(sec-butyl)cyclohex-1-en-1-yl)propanal | Green/watery/sap, floral/lily of the valley |

According to a particular embodiment of the invention, the compounds of formula (I) are 3-[5-(2-propanyl)-1-cyclohexen-1-yl]propanal, 3-[3-(2-propanyl)-1-cyclohexen-1-yl]propanal and the mixture thereof, 3-(5-sec-butyl-1-cyclohexen-1-yl)propanal, 3-[5-ethyl-1-cyclohexen-1-yl]propanal as well as 3-(5-isopropyl-2-methyl-1-cyclohexen-1-yl)propanal.

When the odor of the invention's compounds is compared with that of the prior art cyclohexyl derivatives (for instance 3-(3-isopropylcyclohexyl)propanal, 3-(3-(tert-butyl)cyclohexyl)propanal or 3-(3-isopropylcyclohexyl)butanal, see US and WO references above) and in particular to 3-(3-isopropylcyclohexyl)butanal, then the invention's compounds distinguish themselves by lacking, or not possessing significant, orris, earthy and fatty/aldehyde notes, as well as lacking, or not possessing a significant, powdery undernotes which are characteristic of the prior art compounds. On the other hand, the invention's compound distinguishes from the prior art by having a very strong green note; in particular the invention distinguishes from 3-(3-(tert-butyl)cyclohexyl)propanal by having a dominant green/watery/sap note instead of having a fatty/aldehydic and green/herbaceous connotation (i.e. no watery connotation) which are typical of the prior art. Said differences lend the invention's compounds and the prior art compounds to be each suitable for different uses, i.e. to impart different organoleptic impressions.

As mentioned above, the invention concerns the use of a compound of formula (I) as perfuming ingredient. In other words, it concerns a method or a process to confer, enhance, improve or modify the odor properties of a perfuming composition or of a perfumed article or of a surface, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as butylene or propylene glycols, glycerol, dipropyleneglycol and its monoether, 1,2,3-propanetriyl triacetate, dimethyl glutarate, dimethyl adipate, 1,3-diacetyloxypropan-2-yl acetate, diethyl phthalate, isopropyl myristate, benzyl benzoate, benzyl alcohol, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

As solid carrier it is meant a material where the perfuming composition or some element of the perfuming composition can be chemically or physically bound. In general such solid carrier are employed either to stabilize the composition, either to control the rate of evaporation of the compositions or of some ingredients. The employment of solid carrier is of current use in the art and a person skilled in the art knows how to reach the desired effect. However by way of non-limiting example as solid carriers one may cite absorbing gums or polymers or inorganic material, such as porous polymers, cyclodextrines, wood based materials, organic or inorganic gels, clays, gypsum talc or zeolites.

As other non-limiting example of solid carrier one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation technique. As non-limiting examples one may cite in particular the core-shell encapsulation with resins of the aminoplast, polyamide, polyester, polyurea or polyurethane type or a mixture thereof (all of said resins are well known to a person skilled in the art) using techniques like phase separation process induced by polymerization, by interfacial polymerization, by coacervation or altogether (all of said techniques have been described in the prior art), and optionally in the presence of polymeric stabilizer or a cationic copolymer.

In particular, as resins one may cite the ones produced by the polycondensation of an aldehyde (e.g. formaldehyde, 2,2-dimethoxyethanal, glyoxal, glyoxylic acid or glycolaldehyde and mixtures thereof) with an amine, namely urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

In particular, as resins one may cite the ones produced by the polycondensation of a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins, with aldehydes is represented by articles such as those published by K. Dietrich et al. in Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors and creators have enriched the literature in this field and it would be impossible to cover all published developments here, but the general knowledge in this type of encapsulation is very significant. More recent publications of pertinency, which also address the suitable uses of such microcapsules, are represented for example by the article of H. Y. Lee et al. in Journal of Microencapsulation, 2002, vol. 19, pages 559-569, international patent publication WO 01/41915 or yet the article of S. Bone et al. in Chimia, 2011, vol. 65, pages 177-181.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or *sulphurous* heterocyclic compounds and essential oils, and said perfuming co-ingredients can be of natural or synthetic origin.

In particular one may cite perfuming co-ingredients which are commonly used in perfume formulations, such as:

Aldehydic ingredients: decanal, dodecanal, 2-methyl-undecanal, 10-undecenal, octanal and/or nonenal;

Aromatic-herbal ingredients: eucalyptus oil, camphor, eucalyptol, menthol and/or alpha-pinene;

Balsamic ingredients: coumarine, ethylvanillin and/or vanillin;

Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;

Floral ingredients: Methyl dihydrojasmonate, linalool, Citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-menthanol, Propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-dimdthyldthyl)-1-cyclohexyl acetate, verdyl isobutyrate and/or mixture of methylionones isomers;

Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;

Green ingredients: 2,4-Dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecanedione, pentadecenolide, 3-Methyl-5-cyclopentadecen-1-one, 1,3,4,6,7,8-hexahydro-4,6,6,7,8,8-hexamethylcyclopenta-g-2-benzopyrane, (1S,1'R)-2-[1-(3',3'-dimethyl-1'-cyclohexyl)ethoxy]-2-methylpropyl propanoate, pentadecanolide and/or (1S,1'R)-[1-(3',3'-Dimethyl-1'-cyclohexyl)ethoxycarbonyl]methyl propanoate;

Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, Methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b] furan and any of its stereoisomers, heliotropin, anisic aldehyde, eugenol, cinnamic aldehyde, clove oil, 3-(1,3-benzodioxol-5-yl)-2-methylpropanal and/or 3-(3-isopropyl-1-phenyl)butanal.

According to a particular embodiment, the perfuming composition of the invention comprises perfuming co-ingredients imparting lily of the valley note. As shown in Example 2, the combination of the compound of formula (I) with perfuming co-ingredients of the lily of the valley types allows obtaining a perfuming composition close to Lilial®. Such effect is provided by the combination of floral note of the prior art compounds and green/watery note of the invention's compound. Non limiting examples of perfuming co-ingredients imparting a lily of the valley note can be selected from the group consisting of 3/4-(4-methyl-3-pentenyl)-3-cyclohexene-1-carbaldehyde (origin: Firmenich SA, Geneva, Switzerland), (3,7-dimethyl-6-octenyloxy)acetaldehyde (origin: International Flavors & Fragrances, USA), Bourgeonal® (3-(4-tert-butylphenyl)propanal, trademark from Givaudan-Roure SA, Vernier, Suisse), 1,1-dimethylbenzenepropanol (origin: Firmenich SA, Geneva, Switzerland), Coranol® (4-cyclohexyl-2-methyl-2-butanol; trademark from Firmenich SA, Geneva, Switzerland), 3-(4-Isopropylphenyl)-2-methylpropanal, Cyclosia® Base (7,hydroxyl-3,7-dimethyloctanal, trademark from Firmenich SA, Geneva, Switzerland), Florol® (tetrahydro-2-isobutyl-4-methyl-4(2H)-pyranol, trademark from Firmenich SA, Geneva, Switzerland), Hivernal® (3-(3,3/1,1-dimethyl-5-indanyl)propanal, trademark from Firmenich SA, Geneva, Switzerland), Hydroxycitronellal, Josenol® ((E)-2-methyl-3-(p-tolyl)prop-2-en-1-ol, trademark from Firmenich SA, Geneva, Switzerland), Lilial® (3-(4-tert-butylphenyl)-2-methylpropanal, trademark from Givaudan-Roure SA, Vernier, Suisse), Lilyflore® ((2,5-dimethyl-2,3-dihydro-1H-inden-2-yl)methanol, trademark from Firmenich SA, Geneva, Switzerland), Lyral® (4/3-(4-hydroxy-4-methylpentyl)-3-cyclohexene-1-carbaldehyde, trademark from International Flavors & Fragrances, USA), Mayol® (cis-4-(1methylethyl)-cyclohexanemethanol, trademark from Firmenich SA, Geneva, Switzerland) and 3-(4,4-dimethyl-1-cyclohexen-1-yl)propanal.

A perfumery base according to the invention may not be limited to the above-mentioned perfuming co-ingredients, and many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art. However, one may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), color agents (e.g. dyes and/or pigments) preservative (e.g. antibacterial or antimicrobial or antifungi or anti irritant agents), abrasives, skin cooling agents, fixatives, insect repellents, ointments, vitamins and mixture thereof.

It is understood that a person skilled in the art is perfectly able to design optimal formulations for the desired effect by admixing the above-mentioned components of a perfuming composition, simply by applying the standard knowledge of the art as well as by trial and error methodologies.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modern perfumery, i.e. fine or functional perfumery, to positively impart or modify the odor of a consumer product into which said compound (I) is added. Consequently, another object of the present invention is represented by a perfuming consumer product comprising, as a perfuming ingredient, at least one compound of formula (I), as defined above.

The invention's compound can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises the functional formulation, as well as optionally additional benefit agents, corresponding to the desired consumer product, e.g. a detergent or an air freshener, and an olfactive effective amount of at least one invention's compound. For the sake of clarity, said perfuming consumer product is a non-edible product.

The nature and type of the constituents of the perfuming consumer product do not warrant a more detailed description here, which in any case would not be exhaustive, the skilled person being able to select them on the basis of his general knowledge and according to the nature and the desired effect of said product.

Non-limiting examples of suitable perfuming consumer product can be a perfume, such as a fine perfume, a splash or eau de perfume, a cologne or an shave or after-shave lotion; a fabric care product, such as a liquid or solid detergent, a fabric softener, a fabric refresher, an ironing water, a paper, a bleach, carpet cleaners or curtain-care products; a body-care product, such as a hair care product (e.g. a shampoo, a coloring preparation or a hair spray, a color care product, hair shaping product, a dental care product), a disinfectant, an intimate care product; a cosmetic preparation (e.g. a skin cream or lotion, a vanishing cream, a deodorant or antiperspirant (e.g. a spray or roll on), hair remover, tanning or sun or after sun product, nail products, skin cleansing or a makeup); or a skin-care product (e.g. a perfumed soap, shower or bath mousse, oil or gel, a hygiene product or foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care, a wipe, a dish detergent or hard-surface (e.g. a floor, bath, sanitary or a window) detergent; a leather care product or a car care product, such as a polish, waxes or a plastic cleaners.

Some of the above-mentioned perfuming consumer product may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned products or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 5% by weight, or even more, of the compounds of the invention based on the weight of the composition into which they are incorporated. Concentrations lower than these, such as in the order of 0.01% to 1% by weight, can be used when these compounds are incorporated into perfuming consumer products, percentage being relative to the weight of the article.

The invention's compounds can be prepared according to a method reported in the literature or standard methods known in the art as described herein-below.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 500 MHz machine for $^1H$ and $^{13}C$, the chemical shifts δ are indicated in ppm with respect to TMS as standard, the coupling constants J are expressed in Hz.

Example 1

Synthesis of Compounds of Formula (I)

a) Preparation of a Mixtures of 3-[5-(2-propanyl)-1-cyclohexen-1-yl]propanal and its Isomer 3-[3-(2-propanyl)-1-cyclohexen-1-yl]propanal i) 7-isopropyl-1-oxaspiro[4.5]decan-2-one 3-isopropyl-1-cyclohexanol (140 g; 984 mmol; 2 eq.) was heated in an oil bath at 155° C. under nitrogen. Di-tert-butyl peroxide (18.36 g; 123 mmol; 0.25 eq.) and n-butyl acrylate (63.7 g; 492 mmol; 1 eq.) were added simultaneously and separately over a period of 1 hour. After 4 more hours at 150° C., the reaction was cooled to 50° C. and MTBE (100 mL) was added, followed by 30% aqueous NaOH solution (118 g; 886 mmol). After stirring for 30 minutes, water (140 mL) was added, followed by MTBE (140 mL). The phases were separated and the aq. phase was treated with diethyl ether (2×300 mL) and MTBE (300 mL). Each organic phase was treated with water (210 mL). The combined aqueous phases were treated with 50% aqueous $H_2SO_4$ solution (280 g), extracted twice with diethyl ether. Each organic phase was washed with water, aqueous saturated $NaHCO_3$ solution (carefully), and brine. Combined extracts were dried over sodium sulfate. The product was purified by bulb-to-bulb distillation (100-120° C./0.03 mbar). 7-isopropyl-1-oxaspiro[4.5]decan-2-one was obtained as a 35:65 mixture of diastereoisomers (50.8 g; 98% pure by GC; 254 mmol; 52% yield).

$^1H$ NMR ($CDCl_3$, 500 MHz) (major diastereoisomer): 2.59 (t, J=7 Hz, 2H); 2.12-1.97 (m, 2H); 1.86-1.15 (m, 8H); 0.98-0.84 (m, 2H); 0.88 (d, J=7 Hz, 6H).

$^{13}C$ NMR ($CDCl_3$, 125 MHz) (major diastereoisomer): 176.6 (s); 87.9 (s); 41.2 (d); 40.3 (t); 36.5 (t); 32.4 (d); 30.8 (t); 28.7 (t); 28.1 (t); 22.8 (t); 19.7 (q); 19.6 (q).

ii) 1:1 Mixture of butyl 3-(5-isopropylcyclohex-1-en-1-yl)propanoate and butyl 3-(3-isopropylcyclohex-1-en-1-yl)propanoate 7-isopropyl-1-oxaspiro[4.5]decan-2-one as a 35:65 mixture of diastereoisomers (50.8 g; 254 mmol) was dissolved in n-butanol (34.5 mL). Conc. sulfuric acid (2 g; 20 mmol) was added and the solution was heated under nitrogen in an oil bath at 140° C. during 6 hours. More n-butanol (32.3 mL) was added during the reaction. The reaction was cooled to RT, diluted with water, extracted twice with diethyl ether. Organic phases were washed with aqueous saturated NaHCO$_3$ solution and brine, dried over sodium sulfate. The product was purified by bulb-to-bulb distillation (140° C./0.001 mbar). A 1:1 mixture of isomers butyl 3-(5-isopropylcyclohex-1-en-1-yl)propanoate and butyl 3-(3-isopropylcyclohex-1-en-1-yl)propanoate was obtained as (64 g; 88% pure by GC; 224 mmol; 88% yield).

$^1$H NMR (CDCl$_3$, 500 MHz) (isomer mixture): 5.40 (broad s, 0.5H); 5.32 (s, 0.5H); 4.07 (m, 2H); 2.44-2.39 (m, 2H); 2.30-2.23 (m, 2H); 2.10-1.02 (m, 12H); 0.95-0.83; m; 9H).

$^{13}$C NMR (CDCl$_3$, 125 MHz) (isomer mixture): 173.7 (s); 173.6 (s); 136.5 (s); 136.0 (s); 125.4 (d); 121.3 (d); 64.2 (t); 64.2 (t); 41.8 (d); 40.5 (d); 33.1 (t); 33.1 (t); 33.0 (t); 32.4 (d); 32.4 (t); 32.1 (t); 30.8 (t); 28.6 (t); 25.9 (t); 25.9 (t); 22.5 (t); 19.9 (q); 19.7 (q); 19.6 (q); 19.3 (q); 19.2 (t); 13.7 (q).

iii) 1:1 Mixture of 3-[5-(2-propanyl)-1-cyclohexen-1-yl]propanal and 3-[3-(2-propanyl)-1-cyclohexen-1-yl]propanal Diisobutylaluminum hydride (1 molar in dichloromethane; 311 mL; 311 mmol; 1.4 eq.) was added dropwise to a solution of the 1:1 mixture of isomers butyl 3-(5-isopropylcyclohex-1-en-1-yl)propanoate and butyl 3-(3-isopropylcyclohex-1-en-1-yl)propanoate (56 g; 211 mmol) in dry dichloromethane (250 mL), at −78° C. under nitrogen over a 30 minutes period. At the end of the addition, the reaction was stirred at −78° C. for 2 hours. At this point, a 10% aqueous solution of Na/K-tartrate (500 mL) was added to the reaction at −78° C., which was then warmed up to RT and stirred for 24 hours. The mixture was filtered through celite, rinsing with diethyl ether. Water was added to the filtrate. The mixture was shaken and the phases separated. The organic phase was washed with brine. Each aq. phase was reextracted with diethyl ether. Combined extracts were dried over sodium sulfate. The product was purified by column chromatography (n-heptane/ethyl acetate 25:1) followed by bulb-to-bulb distillation (86° C./1 mbar). A 1:1 mixture of isomers 3-[5-(2-propanyl)-1-cyclohexen-1-yl]propanal and its isomer 3-[3-(2-propanyl)-1-cyclohexen-1-yl]propanal was obtained as (33 g; 99% pure by GC; 181 mmol; 82% yield).

$^1$H NMR (CDCl$_3$, 500 MHz) (isomer mixture): 9.76 (s, 1H); 5.40 (broad s, 0.5H); 5.33 (s, 0.5H); 2.52 (m, 2H); 2.29 (m, 2H); 2.10-1.42 (m, 5H); 1.36-1.27 (m, 1H); 1.22-1.06 (m, 2H); 0.90 (d, J=7 Hz, 1.5H); 0.89 (d, J=7 Hz, 1.5H); 0.87 (m, J=7 Hz; 1.5H); 0.84 (d, J=7 Hz; 1.5H).

$^{13}$C NMR (CDCl$_3$, 125 MHz) (isomer mixture): 202.7 (s); 136.1 (s); 135.6 (s); 125.8 (d); 121.7 (d); 42.0 (t); 41.9 (t); 41.8 (d); 40.4 (d); 32.3 (t); 32.3 (t); 32.3 (d); 30.4 (t); 30.1 (t); 28.7 (t); 25.9 (t); 25.3 (t); 22.4 (t); 19.9 (q); 19.7 (q); 19.6 (q): 19.3 (q).

b) Preparation of (−)-3-[(5S)-5-isopropyl-2-methyl-1-cyclohexen-1-yl]propanal i) 4:1:1 Mixture of (S,E)-3-(5-isopropyl-2-methyl-cyclohex-1-en-1-yl)prop-1-en-1-yl acetate, (E)-3-((1R,5S)-5-isopropyl-2-methylcyclohex-2-en-1-yl)prop-1-en-1-yl acetate and (E)-3-((1S,5S)-5-isopropyl-2-methylcyclohex-2-en-1-yl)prop-1-en-1-yl acetate A mixture of ZnBr$_2$ (0.05 eq, 5 mol %, 7.4 g) and leavo dihydrolimonene (obtained as published for example in the J. Chem. Soc., Chem. Commun. 1994, 24, 2759-2760 or J. Org. Chem. 1982, 10, 1824-1831) (90 g, 0.65 mol) and acrolein diacetate (0.1 eq, 12.0 g, 76 mmol) was heated at 40° C. and acrolein diacetate (1.0 eq, 102 g, 0.645 mol) was then added slowly dropwise over 90 minutes. The temperature was kept <45° C. throughout the introduction.

The solution was stirred at 40° C. for a further 20 hours then diluted with MTBE (300 mL) and washed with water (2×100 mL) then washed cautiously with saturated NaHCO$_3$ solution and brine, dried over anhydrous Na$_2$SO$_4$, then filtered and the solvents removed in vacuo to yield the crude enolacetate as a mixture of isomers. Further purification by vacuum distillation using a short (15 cm) Vigreux column gave the desired enol acetate as a mixture of isomers: (S,E)-3-(5-isopropyl-2-methylcyclohex-1-en-1-yl)prop-1-en-1-yl acetate: (E)-3-((1R,5S)-5-isopropyl-2-methylcyclohex-2-en-1-yl)prop-1-en-1-yl acetate: (E)-3-((1S,5S)-5-isopropyl-2-methylcyclohex-2-en-1-yl)prop-1-en-1-yl acetate (4:1:1, 25.3 g, b.p 80-100° C. at 0.1 mbar in 16% yield).

$^1$H NMR (CDCl$_3$, 500 MHz) (Major isomer) 7.06 (dt, J=12.3 Hz, 1.4, 1H), 5.36 (dt, J=12.3 Hz, 7.41H), 2.71 (dd, J=14.8 Hz, 7.41H), 2.62 (dd, J 14.8 Hz, 7.41H), 2.10 (CH$_3$, 3H), 2.05-1.85 (m, 2H), 1.75-1.65 (m, 3H), 1.61 (s, CH$_3$, 3H), 1.44 (m-6, J=8.4 Hz, 1H), 1.30-1.20 (m, 1H), 1.13 (qd, J=11.9, 5.5 Hz, 1H), 0.87 (d, J=6.9 Hz, CH$_3$, 3H) ppm.

$^{13}$C NMR (CDCl$_3$, 125 MHz) (Major isomer) 168.2 (C=O), 135.7 (CH), 127.6, 127.0 (C), 112.9 (CH), 40.8 (CH$_2$), 33.1 (CH), 32.6 (CH), 32.3 (CH$_2$), 31.3 (CH), 26.5 (CH), 20.7, 19.82, 19.8, 18.6 (CH$_2$) ppm.

ii) 7:1:1 Mixture of (S)-3-(5-isopropyl-2-methylcyclohex-1-en-1-yl)propanal, 3-((1S,5S)-5-isopropyl-2-methylcyclohex-2-en-1-yl)propanal and 3-((1R,5S)-5-isopropyl-2-methylcyclohex-2-en-1-yl)propanal A solution of the enol acetate obtained above (31 g, 132 mmol) and DABCO (5.15 g, 0.35 eq) in methanol (120 mL) was heated at reflux for 7 hours then cooled. The methanol was removed in vacuo then the residue partioned between MTBE and 5% HCl. The organic phase was then washed with water, saturated NaHCO$_3$ solution and brine then dried over Na$_2$SO$_4$ and filtered. The solvents were removed in vacuo to yield the crude aldehyde, 25.2 g as a mixture of isomers, (6:1:1).

Further purification of a portion (18.5 g) by Fischer distillation (120-140° C. at 2.5 to 0.1 mbar) gave mixed fractions plus the desired aldehyde as a mixture (7:1:1) of isomers: (S)-3-(5-isopropyl-2-methylcyclohex-1-en-1-yl) propanal:3-((1S,5S)-5-isopropyl-2-methylcyclohex-2-en-1-yl)propanal:3-((1R,5S)-5-isopropyl-2-methylcyclohex-2-en-1-yl)propanal (7.2 g). (70:15:15 by NMR).

$^1$H NMR (CDCl$_3$, 500 MHz) (Major isomer) 9.78 (t, J=1.9 Hz, 1H), 2.51-2.44 (m, 2H), 2.38-2.25 (m, 2H), 2.04-1.84 (m, 2H), 1.76-1.67 (m, 1H), 1.61 (s, 3H), 1.46 (d, J=6.6 Hz, 1H), 1.44 (d, J=6.6 Hz, 1H), 1.32-1.20 (m, 2H), 1.14 (qd, J=12.2, 5.8 Hz, 1H), 0.89 (d, J=1.8 Hz, 3H) 0.87 (d, J=1.8 Hz, 3H) ppm.

$^{13}$C NMR (CDCl$_3$, 125 MHz) (Major isomer) 202.8 (CH), 127.5, 127.4 (C), 42.6 (CH$_2$), 40.8 (CH), 33.1, 32.6 (CH$_2$), 32.3 (CH), 26.5, 26.1 (CH$_2$), 19.9, 19.8, 18.7 (CH$_3$) ppm.

c) Preparation of 3-[5-ethyl-1-cyclohexen-1-yl]propanal i) Mixture of (5RS,7SR)-7-ethyl-1-oxaspiro[4.5]decan-2-one and (5RS,7RS)-7-ethyl-1-oxaspiro[4.5]decan-2-one 3-ethyl-1-cyclohexanol (123.3 g; 961 mmol; 1.76 eq.) was heated in an oil bath at 155° C. under nitrogen.

Di-tert-butyl peroxide (47.8 g; 320 mmol; 0.59 eq.) and n-butyl acrylate (70.6 g; 546 mmol; 1 eq.) were added simultaneously and separately over a period of 1 hour. After 4 more hours at 150° C., the reaction was cooled to 50° C. and MTBE was added, followed by 30% aqueous NaOH (50 g; 375 mmol). After stirring for 30 minutes, water was added, followed by more MTBE. The phases were separated and the aq. phase was treated with diethyl ether and MTBE. Each organic phase was treated with water. The combined aq. phases were treated with 50% aq. H2SO4, extracted twice with diethyl ether. Each org. phase was washed with water, aqueous saturated NaHCO$_3$, and brine. Combined extracts were dried over sodium sulfate. The product was purified by bulb-to-bulb distillation (80° C./0.1 mbar). It was obtained as a 34:66 mixture of diastereoisomers (40 g; 99.5% pure by GC; 219 mmol; 40% yield).

$^{13}$C-NMR (major diastereoisomer): 176.65 (s); 87.47 (s); 43.03 (t); 36.66 (d); 36.53 (t); 31.08 (t); 30.79 (t); 29.4 (t); 28.72 (t); 22.59 (t); 11.33 (q).

ii) Mixture of butyl 3-(5-ethyl-1-cyclohexen-1-yl) propanoate and butyl 3-(3-ethyl-1-cyclohexen-1-yl) propanoate The lactone obtained above (28.55 g; 157 mmol) was dissolved in n-butanol (40 ml). Concentrated sulfuric acid (0.92 g; 9.4 mmol) was added and the solution was heated under nitrogen in an oil bath at 140° C. More n-butanol (40 ml) was added during the reaction. Total reaction time: 2 days. The reaction was cooled to room temperature, diluted with water, extracted twice with diethyl ether. Organic phases were washed with aqueous saturated NaHCO3 and brine, dried over sodium sulfate. The product was purified by bulb-to-bulb distillation (100° C./0.1 mbar). It was obtained as a 44:56 mixture of isomers (20.4 g; 96% pure by GC; 82 mmol; 52% yield).

$^{13}$C-NMR (regioisomer mixture): 173.68 (s); 173.5 (s); 135.83 (s); 135.70 (s); 126.59 (d); 121.38 (d); 64.14 (t); 37.01 (d); 35.68 (d); 34.78 (t); 33.05 (t); 33.02 (t); 30.77 (t); 29.23 (t); 28.55 (t); 28.41 (t); 25.29 (t); 21.92 (t); 19.20 (t); 19.19 (t); 13.73 (q); 11.47 (q); 11.45 (q).

iii) Mixture of 3-(5-ethyl-1-cyclohexen-1-yl)propanal and 3-(3-ethyl-1-cyclohexen-1-yl)propanal Diisobutylaluminum hydride (1 M in dichloromethane; 120 ml; 120 mmol; 1.2 eq.) was added dropwise to a solution of the ester obtained above (23.87 g; 100 mmol) in dry dichloromethane (200 ml). At the end of the addition, the reaction was stirred at −78° C. for 2 hours. At this point, a 10% aqueous solution of Na/K-tartrate (100 ml) was added to the reaction at −78° C., which was then warmed up to room temperature and stirred for 24 hours. The mixture was filtered through celite, rinsing with diethyl ether. Water was added to the filtrate. The mixture was shaken and the phases separated. The organic phase was washed with brine. Each aqueous phase was reextracted with diethyl ether. Combined extracts were dried over sodium sulfate. The product was purified by column chromatography (n-heptane/MTBE 49:1) followed by bulb-to-bulb distillation (85° C./0.1 mbar). It was obtained as a 39:61 mixture of regioisomers (13.83 g; 95% pure by GC; 79 mmol; 79% yield).

$^{13}$C-NMR (isomer mixture): 202.76 (d); 202.74 (d); 135.44 (s); 135.31 (s); 126.99 (d); 121.73 (d); 41.95 (t); 41.90 (t); 36.97 (d); 35.63 (d); 34.97 (t); 30.16 (t); 30.08 (t); 29.17 (t); 28.73 (t); 28.45 (t); 28.34 (t); 25.25 (t); 21.85 (t); 11.46 (q); 11.43 (q).

d) Preparation of 3-(5-sec-butyl-1-cyclohexen-1-yl)propanal 3-(5-sec-butyl-1-cyclohexen-1-yl)propanal has been synthesized following the experimental part reported in Example 1 a) by replacing 3-isopropyl-1-cyclohexanol by 3-(sec-butyl)-1-cyclohexanol. Following said procedure, 3-(5-sec-butyl-1-cyclohexen-1-yl)propanal has been isolated as a mixture of 2 diastereoisomers.

$^{13}$C NMR (diasteroisomer mixture): 202.83 (s); 135.61 (s); 136.60 (s); 121.97 (d); 121.93 (d); 41.93 (t); 38.95 (d); 38.73 (d); 38.20 (d); 37.94 (d); 29.79 (t); 29.78 (t); 29.49 (t); 29.39 (t); 29.29 (t); 27.56 (t); 27.01 (t); 26.69 (t); 26.43 (t); 25.37 (t); 15.77 (q); 15.38 (q); 11.78 (q); 11.74 (q).

Example 2

Preparation of a Perfuming Composition

A perfuming composition, of the floral type, was prepared by admixing the following ingredients:

| Parts by weight | Ingredient |
|---|---|
| 100 | Acropal [1)] |
| 40 | C 12 Aldehyde |
| 10 | C 8 Aldehyde |
| 50 | 1%* Cuminic aldehyde |
| 20 | (3,7-Dimethyl-6-octenyloxy)acetaldehyde |
| 20 | 9-Undecenal |
| 1000 | Coranol ® [2)] |
| 300 | Hivernal ® [3)] |
| 1000 | 3-(4-Isopropylphenyl)-2-methylpropanal |
| 5000 | Florol ® [4)] |
| 20 | 10%* (4-methylphenoxy)acetaldehyde |
| 500 | Lilyflore ® [5)] |
| 300 | Mayol ® [6)] |
| 500 | (4E)-4-methyl-5-(4-methylphenyl)-4-pentenal |
| 500 | 3 -(4,4-dimethyl-1-cyclohexen-1-yl)propanal |
| 140 | 1%* Trans Decenal |
| 100 | 7-(2-methyl-2-propanyl)-2H-1,5-benzodioxepin-3(4H)-one |
| 9600 | |

*in dipropyleneglycol
[1)] 3/4-(4-methyl-3-pentenyl)-3-cyclohexene-1-carbaldehyde [a)]
[2)] 4-cyclohexyl-2-methyl-2-butanol [a)]
[3)] 3-(3,3/1,1-dimethyl-5-indanyl)propanal [a)]
[4)] tetrahydro-2-isobutyl-4-methyl-4(2H)-pyranol [a)]
[5)] (2,5-dimethyl-2,3-dihydro-1H-inden-2-yl)methanol [a)]
[6)] cis-4-(1methylethyl)-cyclohexanemethanol [a)]
[a)] origin: Firmenich SA, Geneva, Switzerland The addition of 400 parts by weight of a mixture obtained in example 1 a) iii) to the above-described composition imparted to the latter a Lilial® type connotation (trademark from Givaudan SA, Vernier, Switzerland) characterized by the typical floral, green and aqueous-wet Lilial® note. The compound harmonizes very well with and pushes the lily of the valley odorant of the composition (i.e. Hivernal®, (4E)-4-methyl-5-(4-methylphenyl)-4-pentenal and 3-(4,4-dimethyl-1-cyclohexen-1-yl)propanal).

The addition of the same amount of the prior art 3-(3-(tert-butyl)cyclohexyl)propanal instead of the invention's compound provided new fragrance having a more aldehydic character and with less floral/green connotation typical of Lilial®.

The addition of the same amount of the prior art 3-(3-isopropylcyclohexyl)butanal instead of the invention's compound provided new fragrance having a more orris/floral character with a powdery connotation and devoid of the lily of the valley note.

Example 3

Preparation of a Perfuming Composition

A perfume, of the herbaceous, floral lily of the valley type, was prepared by admixing the following ingredients:

| Parts by weight | Ingredient |
|---|---|
| 200 | Hexyl acetate |
| 500 | Isobornyl acetate |
| 100 | Geranyl acetate |
| 100 | Phenylethyl acetate |
| 50 | Styrallyl acetate |
| 400 | Verdyl acetate |
| 500 | Hexylcinnamic aldehyde |
| 100 | 2-Methyl undecanal |
| 50 | Allyl Amyl Glycolate |
| 50 | Methyl anthranilate |
| 40 | Methyl benzoate |
| 250 | Benzylacetone |
| 150 | (1-Methyl-2-phenyl)ethyl butanoate |
| 10 | 7-Isopropyl-2H,4H-1,5-benzodioxepin-3-one |
| 100 | Cetalox ® [1] |
| 30 | Raspberry ketone |
| 50 | Citronellyl Nitrile |
| 250 | Coumarine |
| 30 | Damascone Alpha |
| 600 | Dihydromyrcenol |
| 40 | Ethylvanilline |
| 100 | Eugenol |
| 300 | Fructalate ® [2] |
| 400 | Gamma Undecalactone |
| 200 | Geraniol |
| 500 | Habanolide ® [3] |
| 400 | Hedione ® [4] |
| 100 | Allyl heptanoate |
| 100 | Ionone Beta |
| 300 | Iralia ® [5] |
| 500 | Iso E ® Super [6] |
| 100 | Lavandin Grosso essential oil |
| 20 | 1-(2,2,3,6-Tetramethyl-cyclohexyl)-3-hexanol [a] |
| 30 | Methyl Phenylethyl Ether |
| 50 | 2-Ethyl methylbutyrate |
| 20 | Methylparacresol |
| 30 | Crystal Moss oil |
| 100 | Muscenone ® Delta [7] |
| 20 | Neobutenone ® Alpha [8] |
| 100 | Nirvanol ® [9] |
| 20 | 10%* cis-2-methyl-4-propyl-1,3-oxathiane [a] |
| 300 | Phenylhexanol |
| 250 | Rosinol |
| 500 | Salicynile ® [10] |
| 500 | Sclareolate ® [11] |
| 200 | Terpineol |
| 50 | 2-Ethyl-4,4-dimethylcyclohexanone [a] |
| 50 | 2,4-Dimethyl-3-cyclohexene-1-carbaldehyde |
| 260 | Undecavertol ® [12] |
| 500 | 2-Tert-butyl-1-cyclohexyl acetate |
| 100 | Yara Yara |
| 9700 | |

*in dipropyleneglycol
[1] dodecahydro-3a,6,6,9a-tetramethyl-naphtho[2,1-b]furan [a]
[2] diethyl 1,4-cyclohexane dicarboxylate [a]
[3] pentadecenolide [a]
[4] methyl dihydrojasmonate [a]
[5] mixture of methylionones isomers [a]
[6] 1-(octahydro-2,3,8,8-tetramethyl-2-naphtalenyl)-1-ethanone [c]
[7] 3-methyl-5-cyclopentadecen-1-one [a]
[8] 1-(5,5-dimethyl-1-cyclohexen-1-yl)-4-penten-1-one [a]
[9] 3,3-dimethyl-5-(2,2,3-trimethyl-3-cyclopenten-1-yl)-4-penten-2-ol [a]
[10] (2Z)-2-phenyl-2-hexenenitrile [a]
[11] propyl (S)-2-(1,1-dimethylpropoxy)propanoate [a]
[12] 4-methyl-3-decen-5-ol [b]
[a] origin: Firmenich SA, Geneva, Switzerland
[b] origin: Givaudan-Roure SA, Vernier, Suisse
[c] origin: International Flavors & Fragrances, USA The addition of 300 parts by weight of a mixture obtained in example 1 a) iii) to the above-described composition imparted to the latter a unique fresh-green and floral connotation pushing the lily of the valley and citrus tonality, with a more powerful impact.

The invention claimed is:

1. A perfuming ingredient that imparts green floral odor notes to a perfuming composition or perfumery consumer product to which it is added, the perfuming ingredient comprising a compound of formula (I)

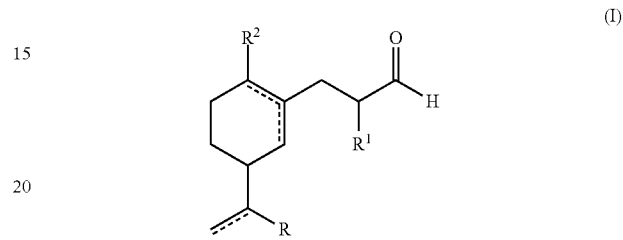

in the form of any one of its stereoisomers or a mixture thereof, and wherein the exocyclic dotted line represents a carbon-carbon single or double bond, and one endocyclic dotted line represents a carbon-carbon single bond and the other endocyclic dotted line represents a carbon-carbon double bond; and R, $R^1$ and $R^2$ represent, independently from each other, a hydrogen atom or a $C_{1-3}$ alkyl group.

2. The perfuming ingredient of claim 1, characterized in that said R is a methyl group.

3. The perfuming ingredient of claim 1, characterized in that $R^1$ is a hydrogen atom or methyl group.

4. The perfuming ingredient of claim 1, characterized in that $R^2$ is a hydrogen atom or a methyl group.

5. The perfuming ingredient of claim 1, characterized in that the compound is 3-[5-(2-propanyl)-1-cyclohexen-1-yl]propanal and/or its isomer 3-[3-(2-propanyl)-1-cyclohexen-1-yl]propanal.

6. A perfuming composition comprising
   i) at least one compound of formula (I) as defined in claim 1;
   ii) at least one ingredient selected from the group consisting of a perfumery carrier and a perfumery base; and
   iii) optionally at least one perfumery adjuvant.

7. A perfuming consumer product comprising at least one compound of formula (I) as defined in claim 1.

8. A perfuming consumer product according to claim 7, characterized in that the perfumery consumer product is a perfume, a fabric care product, a body-care product, a cosmetic preparation, a skin-care product, an air care product or a home care product.

9. A perfuming consumer product according to claim 7, characterized in that the perfumery consumer product is a fine perfume a splash or eau de perfume, a cologne, an shave or after-shave lotion, a liquid or solid detergent, a fabric softener, a fabric refresher, an ironing water, a paper, a bleach, a carpet cleaners, curtain-care products, a shampoo, a coloring preparation, a color care product, a hair shaping product, a dental care product, a disinfectant, an intimate care product, a hair spray, a vanishing cream, a deodorant or antiperspirant, hair remover, a tanning or sun product, nail products, skin cleansing, a makeup, a perfumed soap, shower or bath mousse, oil or gel, foot/hand care products, a hygiene product, an air freshener, a "ready to use" powdered air freshener, a mold remover, furnisher care, wipe, a dish detergent, a hard-surface detergent, a leather care product or a car care product.

10. A method to confer, enhance, improve or modify the green floral odor properties of a perfuming composition or of a perfumed article, which method comprises adding to said composition or article an effective amount of at least a compound of formula (I):

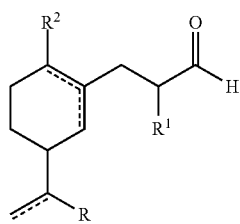

(I)

in the form of any one of its stereoisomers or a mixture thereof, and wherein the exocyclic dotted line represents a carbon-carbon single or double bond, and one endocyclic dotted line represents a carbon-carbon single bond and the other endocyclic dotted line represents a carbon-carbon double bond; and R, $R^1$ and $R^2$ represent, independently from each other, a hydrogen atom or a $C_{1-3}$ alkyl group.

11. The method of claim 10, wherein the R of the compound of formula (I) is a methyl group.

12. The method of claim 10, wherein the $R^1$ of the compound of formula (I) is a hydrogen atom or methyl group.

13. The method of claim 10, wherein the $R^2$ of the compound of formula (I) is a hydrogen atom or a methyl group.

14. The method of claim 10, wherein the compound is 3-[5-(2-propanyl)-1-cyclohexen-1-yl]propanal and/or its isomer 3-[3-(2-propanyl)-1-cyclohexen-1-yl]propanal.

15. The method of claim 10, wherein the compound is added to a perfuming composition comprising at least one ingredient selected from the group consisting of a perfumery carrier and a perfumery base.

16. The method of claim 10, wherein the compound is added to a perfuming composition comprising at least one ingredient selected from the group consisting of a perfumery carrier and a perfumery base along with at least one perfumery adjuvant.

17. The method of claim 10, wherein the compound is added to a perfuming consumer product that is a perfume, a fabric care product, a body-care product, a cosmetic preparation, a skin-care product, an air care product or a home care product.

18. The method of claim 10, wherein the compound is added to a perfumery consumer product that is a fine perfume a splash or eau de perfume, a cologne, an shave or after-shave lotion, a liquid or solid detergent, a fabric softener, a fabric refresher, an ironing water, a paper, a bleach, a carpet cleaners, curtain-care products, a shampoo, a coloring preparation, a color care product, a hair shaping product, a dental care product, a disinfectant, an intimate care product, a hair spray, a vanishing cream, a deodorant or antiperspirant, hair remover, a tanning or sun product, nail products, skin cleansing, a makeup, a perfumed soap, shower or bath mousse, oil or gel, foot/hand care products, a hygiene product, an air freshener, a "ready to use" powdered air freshener, a mold remover, furnisher care, wipe, a dish detergent, a hard-surface detergent, a leather care product or a car care product.

* * * * *